US010716460B2

(12) United States Patent
Jessop

(10) Patent No.: US 10,716,460 B2
(45) Date of Patent: *Jul. 21, 2020

(54) STEREOSCOPIC VIDEO IMAGING AND TRACKING SYSTEM

(71) Applicant: Ultradent Products, Inc., South Jordan, UT (US)

(72) Inventor: Neil T. Jessop, Sandy, UT (US)

(73) Assignee: Ultradent Products, Inc., South Jordan, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 16/192,597

(22) Filed: Nov. 15, 2018

(65) Prior Publication Data

US 2019/0099068 A1 Apr. 4, 2019

Related U.S. Application Data

(63) Continuation of application No. 15/365,551, filed on Nov. 30, 2016, now Pat. No. 10,154,775, which is a (Continued)

(51) Int. Cl.
*G01B 11/03* (2006.01)
*A61B 1/00* (2006.01)
(Continued)

(52) U.S. Cl.
CPC ...... *A61B 1/00193* (2013.01); *A61B 1/00045* (2013.01); *A61B 1/00188* (2013.01);
(Continued)

(58) Field of Classification Search
CPC . A61B 1/00193; A61B 1/00045; A61B 1/247; A61B 1/045; A61B 1/00188;
(Continued)

(56) References Cited

U.S. PATENT DOCUMENTS 5,123,726 A 6/1992 Webster
5,124,797 A 6/1992 Williams et al.
(Continued)

FOREIGN PATENT DOCUMENTS

FR 2699296 6/1994
GB 2329545 3/1999
(Continued)

OTHER PUBLICATIONS

Heacock et al., Viewing Ocular Tissues with A Stereoscopic Endoscope Coupled to a Head Mounted Display (HMD), http://www.hitl.washington.edu/publications/heacock; 9 pages as accessed Feb. 12, 2010.
(Continued)

*Primary Examiner* — Howard D Brown, Jr.
(74) *Attorney, Agent, or Firm* — Thorpe North & Western, LLP

(57) ABSTRACT

Systems and methods for viewing stereoscopic video images are disclosed. In one example, a stereoscopic video imaging and tracking system can include a first video camera to generate a first video feed of a subject; and a second video camera spaced a distance from the first video camera to generate a second video feed of the subject, wherein the first video camera and the second video camera are directed toward a convergent point to provide a stereoscopic image of the subject. The system can also include a tracking system to cause the first video camera and the second video camera to follow a tracking point to maintain stereopsis of the subject. A head mountable video display can be present to display the stereoscopic image.

40 Claims, 7 Drawing Sheets

Related U.S. Application Data continuation of application No. 13/989,284, filed as application No. PCT/US2011/062667 on Nov. 30, 2011, now Pat. No. 9,545,188.

(60) Provisional application No. 61/419,186, filed on Dec. 2, 2010.

(51) Int. Cl.
| | |
|---|---|
| H04N 13/246 | (2018.01) |
| H04N 13/296 | (2018.01) |
| H04N 13/344 | (2018.01) |
| H04N 13/239 | (2018.01) |
| A61B 1/045 | (2006.01) |
| A61B 1/247 | (2006.01) |

(52) U.S. Cl.
CPC .............. *A61B 1/045* (2013.01); *A61B 1/247* (2013.01); *H04N 13/239* (2018.05); *H04N 13/246* (2018.05); *H04N 13/296* (2018.05); *H04N 13/344* (2018.05)

(58) Field of Classification Search
CPC .. H04N 13/239; H04N 13/344; H04N 13/296; H04N 13/246; H04N 13/0239; H04N 2005/2255; H04N 13/0296; H04N 13/0055

See application file for complete search history.

(56) References Cited

U.S. PATENT DOCUMENTS

| | | | |
|---|---|---|---|
| 5,151,722 A | 9/1992 | Massof et al. | |
| 5,539,422 A | 7/1996 | Heacock et al. | |
| 5,543,816 A | 8/1996 | Heacock | |
| 5,662,111 A | 9/1997 | Cosman | |
| 5,774,096 A | 6/1998 | Usuki et al. | |
| 5,825,540 A | 10/1998 | Gold et al. | |
| 5,848,967 A | 12/1998 | Cosman | |
| 5,864,360 A | 1/1999 | Okauchi et al. | |
| 5,898,520 A | 4/1999 | Curatu | |
| 5,917,460 A | 6/1999 | Kodama | |
| 5,961,456 A | 10/1999 | Gildenberg | |
| 5,991,085 A * | 11/1999 | Rallison | G02B 27/017 345/8 |
| 6,006,126 A | 12/1999 | Cosman | |
| 6,219,186 B1 | 4/2001 | Hebert | |
| 6,275,725 B1 | 8/2001 | Cosman | |
| 6,326,994 B1 | 12/2001 | Yoshimatsu | |
| 6,351,661 B1 | 2/2002 | Cosman | |
| 6,396,627 B1 | 5/2002 | Tachihara et al. | |
| 6,405,072 B1 | 6/2002 | Cosman | |
| 6,414,708 B1 | 7/2002 | Carmeli et al. | |
| 6,480,174 B1 | 11/2002 | Kaufmann et al. | |
| 6,675,040 B1 | 1/2004 | Cosman | |
| 6,856,314 B2 | 2/2005 | Ng | |
| 6,900,777 B1 | 5/2005 | Herbert et al. | |
| 7,436,568 B1 | 10/2008 | Kuykendall, Jr. | |
| 8,477,175 B2 | 7/2013 | Shaffer et al. | |
| 8,564,641 B1 * | 10/2013 | Levin | H04N 13/111 348/42 |
| 8,939,894 B2 | 1/2015 | Morrissette et al. | |
| 9,545,188 B2 | 1/2017 | Jessop | |
| 2002/0024675 A1 * | 2/2002 | Foxlin | G02B 27/017 356/620 |
| 2002/0075201 A1 * | 6/2002 | Sauer | G02B 27/017 345/7 |
| 2002/0080094 A1 | 6/2002 | Biocca et al. | |
| 2003/0067536 A1 | 4/2003 | Boulanger et al. | |
| 2003/0207227 A1 | 11/2003 | Abolfathi | |
| 2004/0138556 A1 | 7/2004 | Cosman | |
| 2004/0224279 A1 | 11/2004 | Siemons | |
| 2004/0238732 A1 | 12/2004 | State et al. | |
| 2005/0020910 A1 | 1/2005 | Quadling et al. | |
| 2005/0248852 A1 | 11/2005 | Yamasaki | |
| 2006/0082647 A1 | 4/2006 | Donomae et al. | |
| 2007/0121203 A1 * | 5/2007 | Riederer | G02B 27/0172 359/377 |
| 2008/0228438 A1 | 9/2008 | Lin | |
| 2008/0239080 A1 | 10/2008 | Moscato | |
| 2009/0187389 A1 | 7/2009 | Dobbins et al. | |
| 2009/0213114 A1 | 8/2009 | Dobbins et al. | |
| 2009/0228841 A1 | 9/2009 | Hildreth | |
| 2010/0013739 A1 | 1/2010 | Sako et al. | |
| 2010/0225735 A1 | 9/2010 | Shaffer | |
| 2010/0231734 A1 | 9/2010 | Cai | |
| 2010/0253917 A1 | 10/2010 | Gao et al. | |
| 2011/0046483 A1 * | 2/2011 | Fuchs | A61B 8/4416 600/439 |
| 2011/0050547 A1 | 3/2011 | Mukawa | |
| 2011/0102549 A1 | 5/2011 | Takahashi | |
| 2012/0019623 A1 | 1/2012 | Kokuwa et al. | |
| 2012/0025975 A1 | 2/2012 | Richey et al. | |
| 2012/0050476 A1 | 3/2012 | Kawaguchi et al. | |
| 2012/0069143 A1 | 3/2012 | Chu | |
| 2013/0042296 A1 | 2/2013 | Hastings et al. | |
| 2013/0060146 A1 | 3/2013 | Yang et al. | |
| 2013/0201276 A1 | 8/2013 | Pradeep et al. | |
| 2013/0250067 A1 | 9/2013 | Laxhuber et al. | |
| 2014/0152550 A1 | 6/2014 | Beall et al. | |
| 2015/0156461 A1 * | 6/2015 | Jessop | H04N 7/18 348/47 |
| 2016/0148052 A1 * | 5/2016 | Tsuda | G02B 27/017 345/633 |
| 2016/0154620 A1 * | 6/2016 | Tsuda | G06F 19/3481 345/633 |
| 2016/0191887 A1 | 6/2016 | Casas | |

FOREIGN PATENT DOCUMENTS

| | | |
|---|---|---|
| JP | H07023429 | 1/1995 |
| JP | H10-210506 A | 8/1998 |
| JP | 2000163558 | 6/2000 |
| JP | 2000-338416 A | 12/2000 |
| JP | 2002142233 | 5/2002 |
| JP | 2002232913 | 8/2002 |
| JP | 2004057614 | 2/2004 |
| JP | 2005051472 | 2/2005 |
| JP | 2006-142001 A | 6/2006 |
| JP | 2007518540 | 7/2007 |
| JP | 2007275202 | 10/2007 |
| JP | 2009153785 | 7/2009 |
| JP | 2011104186 | 6/2011 |
| JP | 2012015661 | 1/2012 |
| KR | 20090041843 | 4/2009 |
| WO | 03081831 | 10/2003 |
| WO | 2005070319 | 8/2005 |
| WO | 2005093687 | 10/2005 |
| WO | 2007066249 | 6/2007 |
| WO | 2007111570 | 10/2007 |
| WO | 2012075155 | 6/2012 |

OTHER PUBLICATIONS

Mora, Vison 3-D System given test-run at LLUSD, LLU School of Dentistry—Newsletter, Apr. 20, 2009; 2 pages.

Ostrovsky, EndoSite 3Di Digital Vision System, Viking Systems Inc., Mar. 22, 2005, Medgadget LLC, 3 pages.

Iannizzotto et al.; "A Multimodal Perceptual User Interface for Video-Surveillance Environments;" In Proceedings of the 7th International Conference on Multimodal Interfaces, ICMI 2005; (Oct. 4-6, 2005); pp. 45-52; Trento, Italy; Association for Computing Machinery.

* cited by examiner

STEREOSCOPIC VIDEO IMAGING AND TRACKING SYSTEM

The present application is a continuation of U.S. patent application Ser. No. 15/365,551, filed on Nov. 30, 2016, which is a continuation of U.S. patent application Ser. No. 13/989,284, filed on Aug. 1, 2013, now U.S. Pat. No. 9,545,188, issued Jan. 17, 2017, which is a national stage application of PCT/US2011/062667, filed on Nov. 30, 2011, which claims the benefit of U.S. Provisional Patent Application No. 61/419,186, filed on Dec. 2, 2010, each of which is incorporated herein by reference.

BACKGROUND

Significant technological advancements have been made in the practice of dentistry. These advancements have enable better patient care as well decreased anxiety for patients when visiting a dentist.

Many techniques now used by dentists to provide advanced care involve the ability to see and focus on very small details in a patient's mouth. Glasses with magnification loops are often used by dentists to increase their ability to view fine details. The glasses can be expensive and heavy, becoming burdensome for a dentist to wear for long periods of time. In addition, the magnification loops can cause eye strain and tunnel vision, reducing a dentist's ability to see both the magnified area and the surrounding area simultaneously.

Additionally, to obtain a desired view of the areas within a patient's intraoral cavity, a dentist often has to lean forward and hunch. Such posture can cause long term health problems for a dentist. Dentists that do not take precautionary measures regarding their posture can have their careers cut short or limited by back pain and other associated back problems. In addition, these injuries can significantly affect a dentist's quality of life outside of the dental office.

BRIEF DESCRIPTION OF THE DRAWINGS

Features and advantages of the present disclosure will be apparent from the following detailed description, taken in conjunction with the accompanying drawings, which together illustrate, by way of example, features of the invention.

Figure 1A:
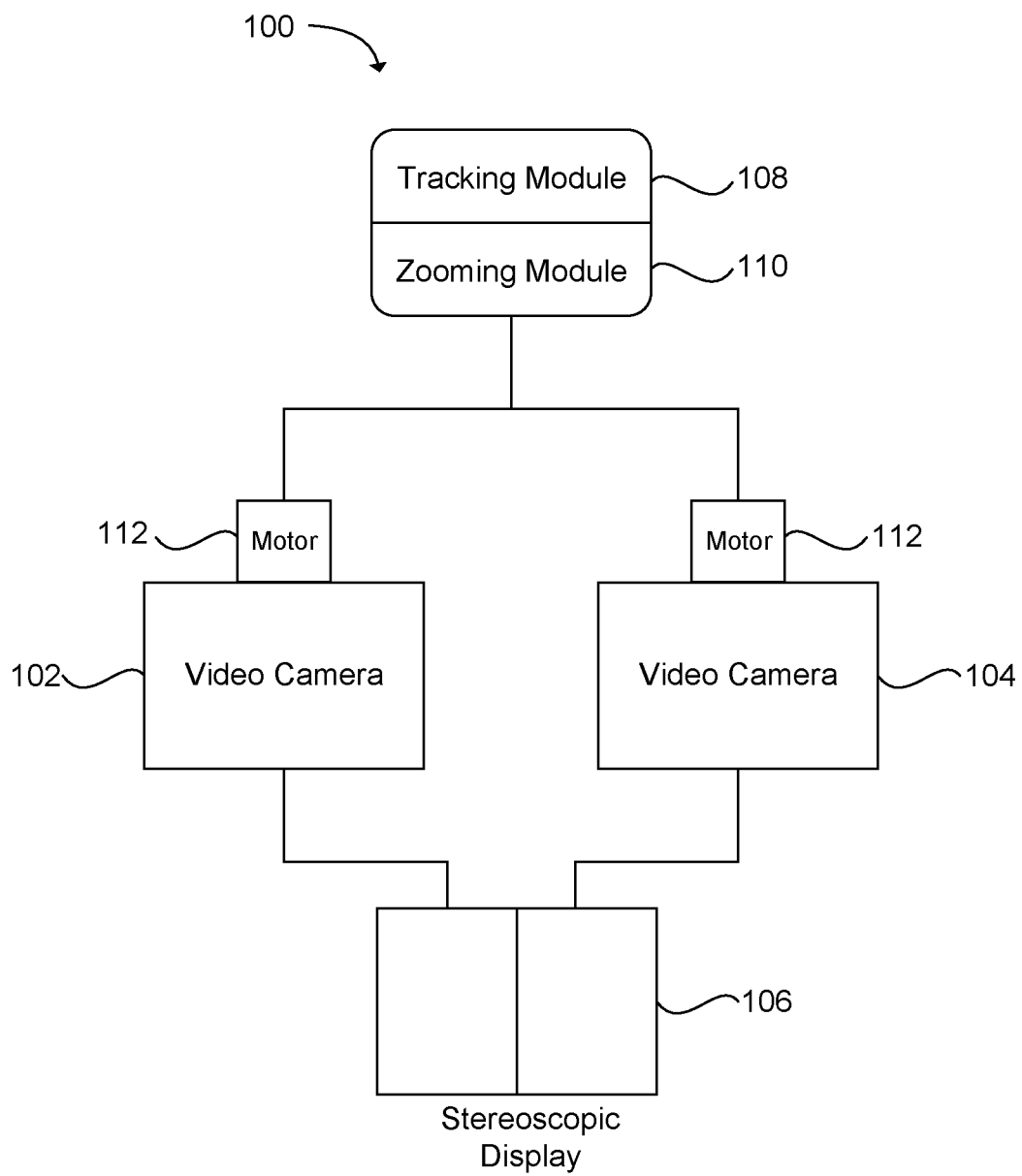
FIG. 1a illustrates a block diagram of a system for viewing stereoscopic video images in accordance with an embodiment of the present disclosure.

Reference will now be made to the illustrated exemplary embodiments, and specific language will be used herein to describe the same. It will nevertheless be understood that no limitation of the scope of the invention is thereby intended.

DETAILED DESCRIPTION

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular embodiments only and is not intended to be limiting.

As a preliminary matter, it is noted that much discussion is related herein to the dental profession and conducting dental exams and procedures. However, this is done for exemplary purposes only, as the systems and methods described herein are also applicable to other medical professionals that would benefit from high magnification stereoscopic imaging and tracking of a desired site for surgery or examination. For example, the systems and methods herein can be especially useful in imaging locations where movement may occur, such as with minimally invasive surgeries when a patient is awake and moving or with examination of sites of interest of an alert patient. Additionally, the systems and methods of the present disclosure can also be applicable to viewing and tracking in the manner described herein that is outside of the medical professions generally, e.g., research, teaching, microbiology, electronics, jewel cutting, watch repair, etc.

With this in mind, an initial overview of technology embodiments is provided below and then specific technology embodiments are described in further detail thereafter. This initial description is intended to provide a basic understanding the technology, but is not intended to identify all features of the technology, nor is it intended to limit the scope of the claimed subject matter.

A dentist's ability to view a patient's intraoral cavity in detail is valuable for proper diagnosis of dental issues and performance of dental work in general. A magnified view of locations within the intraoral cavity can enable a dentist to adequately provide the advanced and complex solutions that are now available to patients. However, a typical solution to obtain a magnified view is through the use of glasses with one or more magnification loops. The use of magnification loops can strain a dentist's eyes and increase drowsiness. In addition, a dentist may need to lean forward and/or slouch in order to obtain a desired viewing angle inside of a patient's mouth. Over long periods of time, this can cause problems with posture, back pain, and debilitating physical damage to a dentist's back. Back pain and injury can reduce the length of the dentist's career and negatively affect the quality of his or her life outside of the dentist's office.

In accordance with one embodiment of the present disclosure, a system and method for viewing stereoscopic video images is disclosed. The system and method enable a dentist to obtain a desired view of a patient's intraoral cavity while reducing eye strain and enabling the dentist to maintain a proper posture. It is noted that in other fields, such as medicine, electronics, teaching, microbiology, or any other field where high magnification stereoscopic vision may be useful, the systems and methods of the present disclosure are equally applicable. Thus, discussion of dentistry is for exemplary purposes only and is not considered limiting except as specifically set forth in the claims.

That being said, in order to provide a desired level of care to patients, a hygienist, dentist, oral surgeon, or other type of dental professional should be able to delicately and accurately move dental tools in a desired direction. Typically, two dimensional images can make it challenging to accurately move dental equipment within a patient's intraoral cavity. The use of a stereoscopic image enables stereopsis to be maintained, thereby allowing a medical professional to perceive depth, enabling dental equipment to be accurately moved in a desired direction while viewing the stereoscopic image. As used herein, the term "stereopsis" refers to the process in visual perception leading to the sensation of depth from viewing two optically separated projections of the world projected onto a person's two eyes, respectively.

In addition, the systems and methods disclosed herein enable multiple persons viewing the stereoscopic video image to view a selected area from the same perspective. For instance, a dentist and a dental assistant can each view the same stereoscopic video image of a location such as a tooth or an area around a tooth in a patient's mouth. The capability for both the dentist and the dental assistant to view a stereoscopic video image of the area from the same perspective can significantly enhance the ability of the dental assistant to assist the dentist as needed. Moreover, the image may also be viewed by additional persons such as the patient or dental school students. The ability of the patient to view the same image as the dentist can enable the dentist to better educate the patient as to the condition of his or her teeth, and the procedures that will be conducted. Viewing the stereoscopic image can significantly enhance student's ability to learn and understand the teachings of their instructor from his or her viewpoint.

In accordance with one embodiment of the present invention, a system 100 for viewing stereoscopic dental video images is disclosed, as provided in the example illustration of FIG. 1a. The system comprises a first video camera 102 configured to be directed toward and create a first video feed of a patient's intraoral cavity. A second video camera 104 can be horizontally spaced a selected distance from the first video camera 102. In one embodiment, the horizontal spacing can simulate the spacing between a person's eyes in order to produce a first video feed and a second video feed that can be displayed to simulate a person's vision from his or her left eye and right eye. This spacing is referred to as the pupilary distance. A typical pupilary distance is from about 50 millimeters (mm) to about 75 mm. Alternatively, the cameras may be spaced a greater distance apart, while optically compensating for the greater distance to produce a similar image as the cameras spaced a pupilary distance apart.

The system 100 further comprises a stereoscopic video display 106. In one embodiment, the stereoscopic display can be a head mountable stereoscopic display with a right video display viewable by a person's right eye and a left video display viewable by a person's left eye. By displaying the first and second video feeds in the left and right video displays, a near real-time stereoscopic video image is created.

The stereoscopic video image provides a visual perception leading to the sensation of depth from the two slightly different video images projected onto the retinas of the person's two eyes. This visual perception leading to the sensation of depth is referred to as stereopsis. No additional video or computer processing of the first and second video images may be needed when using the head mountable stereoscopic display. The sensation of depth is created due to the differing projections of the first and second cameras that are separated by, for example, a pupilary distance.

The ability to perceive depth can be valuable to a dentist that is working with a patient. Proper depth perception enables the dentist to make small, but critical movements when performing dentistry. Previously, the lack of ability to display depth perception has limited the use of cameras and display screens in the practice of dentistry. With the use of two separate cameras that are configured to provide a display with stereopsis, a dentist can view the resulting stereoscopic display that provides the sensation of depth, thereby enabling the dentist to maintain substantially the same hand-eye coordination that the dentist has learned during his or her practice using loops or other magnification systems.

In one embodiment, the first video feed from the first video camera 102 and the second video feed from the second video camera 104 can be communicated to the stereoscopic video display 106 through wired communication cables, such as a digital visual interface (DVI) cable, a high-definition multimedia interface (HDMI) cable, component cables, and so forth.

Figure 1B:
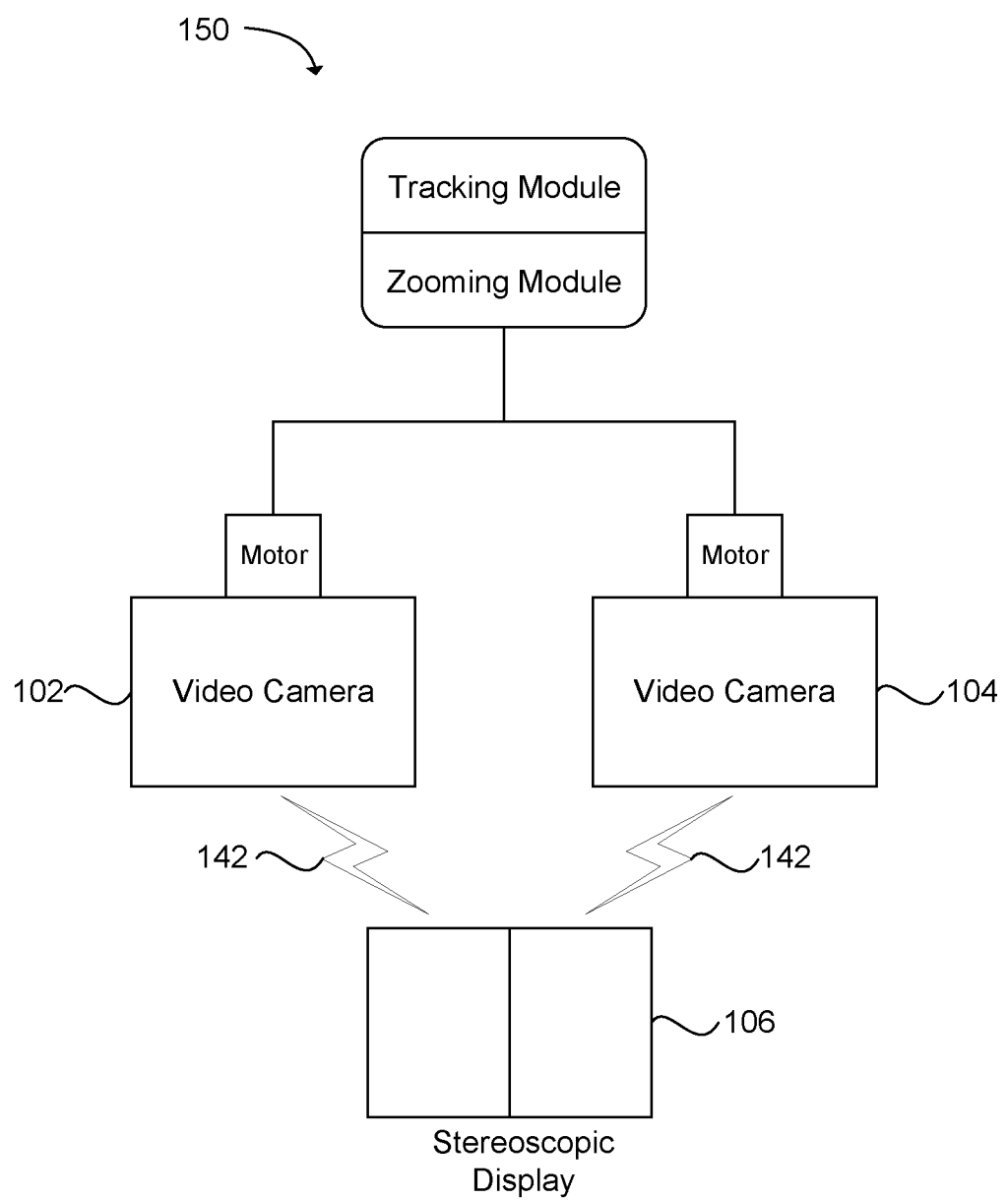
FIG. 1b illustrates a block diagram of a system for viewing stereoscopic video images with a wireless data link in accordance with an embodiment of the present disclosure.

Alternatively, the information from the first video feed and the second video feed can be communicated wirelessly to the stereoscopic video display 106. For instance, FIG. 1b shows a system 150 that provides a wireless data link 142 between the video display 106 and each of the first video camera 102 and the second video camera 104.

Figure 1C:
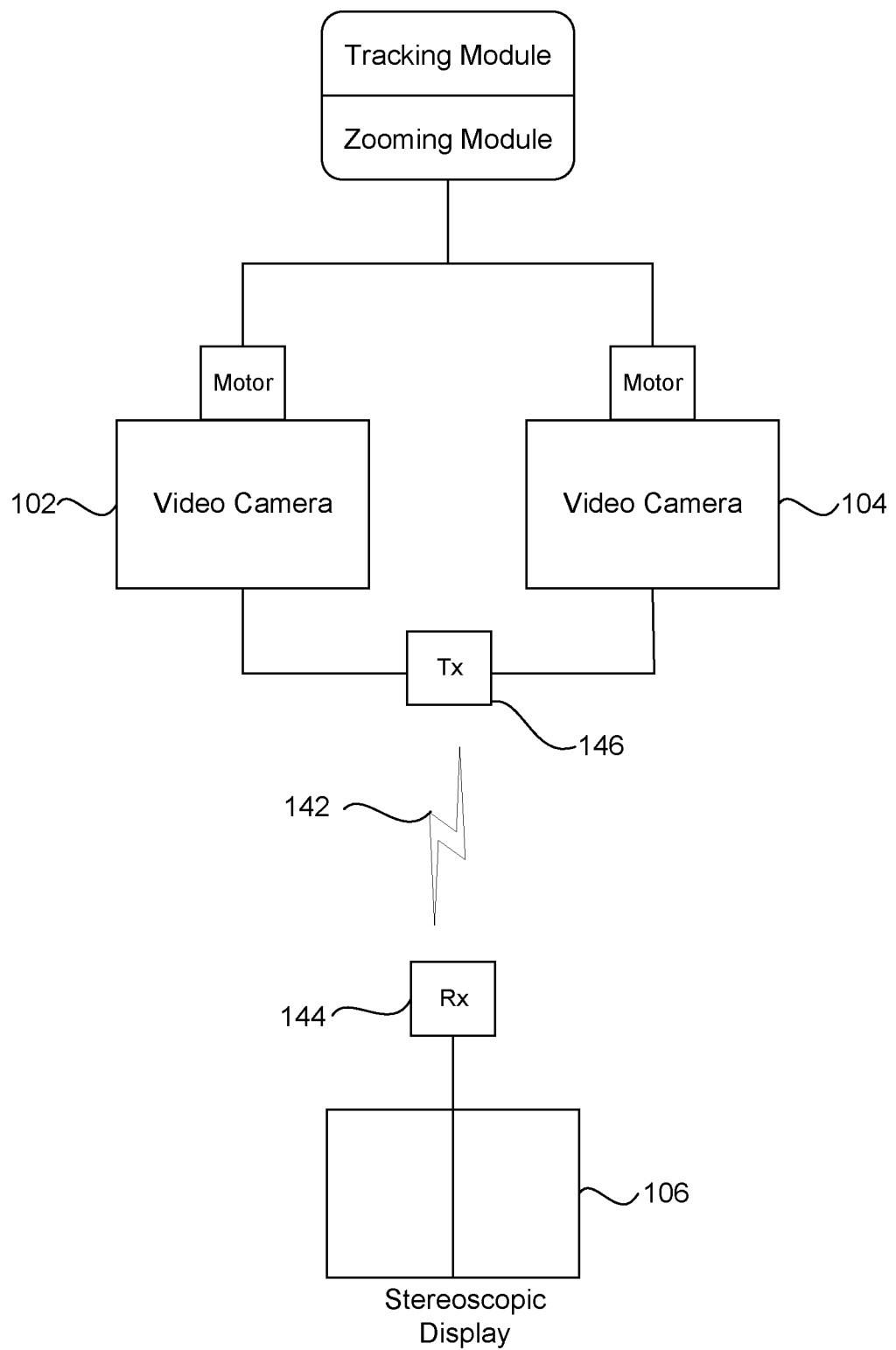
FIG. 1c illustrates a block diagram of a system for viewing stereoscopic video images with a wireless data link comprising a single transmitter and receiver in accordance with an embodiment of the present disclosure.

An alternative embodiment is displayed in FIG. 1c, wherein the first and second video feeds are communicated via a wired connection to a single transmitter 146. The transmitter can wirelessly communicate 142 the first and second video feeds from the first and second video cameras 102, 104, respectively, to the video display 106. A wireless receiver 144 at the video display can be used to receive the first and second video feeds from the transmitter and communicate the video feeds to the video display.

Various standards being developed to wirelessly communicate video feeds include the WirelessHD standard, the Wireless Gigabit Alliance (WiGig), the Wireless Home Digital Interface (WHDI), the Institute of Electronics and Electrical Engineers (IEEE) 802.15 standard, and the standards developed using ultrawideband (UWB) communication protocols. One or more wireless standards that enable the video feed information from the first and second video feeds to be transmitted to the stereoscopic video display can be used to eliminate the use of wires and free the user to move about more freely. This can be especially useful when the stereoscopic video display 106 is head mountable.

Returning to FIG. 1a, the system 100 can also include a tracking module 108 that is in communication with the first video camera 102 and the second video camera 104. The tracking module is configured to cause the first video camera and the second video camera to be directed to a desired convergent point relative to a selected tracking point.

The tracking point can be a selected location on or about the patient's body that enables the cameras 102, 104 to be redirected relative to the motion of the tracking point. For instance, the tracking point may be a location on the patient's head. When the patient moves his or her head, the cameras can move with the patient so that the image on the display screen is not substantially changed due to movements of the patient. Alternatively, the tracking point may be located at or about a dental patient's intraoral cavity. For instance, the tracking point may be located on a tooth, a dental tool, or on a dental retractor located in or about the patient's intraoral cavity.

The tracking point can be any type device or object that enable the movement of the patient to be tracked relative to the position of the cameras. For instance, tracking may be accomplished using radio frequency triangulation. Multiple tracking transceivers can be located on or about the patient. A marker, such as a tool, can also include a transceiver. The location of the tool relative to the location of the markers can be calculated based on the timing of the arrival of tracker signals transmitted from the tool transceiver at the tracking transceivers. The location of the tool transceiver can be calculated using trigonometry, as can be appreciated.

In another embodiment, the tracking point may be an optically trackable marker such as a reflective dot or an optical dot formed using a different colored light or an infrared light source. The light sources for the colored light or the infrared light may be one or more light emitting diodes or lasers. The tracking module can include image recognition software that enables the cameras to be substantially directed relative to the optically trackable marker. Alternatively, an infrared receiver can be used to track a location of an infrared optical dot.

In another embodiment, image recognition software may be used that can recognize a location or feature, such as a person's nostrils, eyes, or other distinct characteristics. As the person's selected feature moves, the position of the camera can be adjusted to maintain the stereoscopic video image of a selected area within the person's intraoral cavity. The ability to adjust a direction of the video cameras relative to movement of the patient can enable the video cameras to provide a relatively high amount of magnification of a desired location within the intraoral cavity.

Accordingly, the system can also include a zooming module 110. The zooming module can be in communication with the first video camera 102 and the second video camera 104. The zooming module can be configured to provide a desired magnification of the near real-time stereoscopic video image. As previously discussed, the ability to view a desired location with a selected magnification provides a significant advantage to a dentist to conduct complex and detailed procedures. Dentists typically use glasses with magnification loops to magnify images in the order of about 4 times. However, in accordance with embodiments of the present disclosure, zooming ranges are only limited by the zooming range of the first and second video camera.

In one specific embodiment, the video cameras 102, 104 can be configured to provide a magnification from one time to over 20 times a standard image, or more. The magnification may be achieved either through the use of an optical magnification, a digital zoom, or a combination of the two. The stereoscopic display can provide a clear, focused image of the desired location within the patient's intraoral cavity at a high magnification. The video cameras can be set at substantially the same magnification to enable the visual perception leading to a sensation of depth to be maintained. In addition, the rate at which the cameras change magnification can be substantially the same to maintain stereopsis of the stereoscopic video image as the image is zoomed in and out using the zooming module to communicate with the first and second video cameras.

In one embodiment, the first and second video cameras 102, 104 and the stereoscopic display 106 can be configured to display a relatively high resolution. For instance, the cameras and display can be configured to provide a 720P progressive video display with 1280 by 720 pixels (width by height), a 1080i interlaced video display with 1920×1080 pixels, or a 1080p progressive video display with 1920×1080 pixels. As processing power and digital memory continue to exponentially increase in accordance with Moore's Law, the cameras and display may provide an even higher resolution, such as 4320P progressive video display with 7680×4320 pixels. With higher resolution, an image can be magnified using software (digital zoom) to provide a digital magnification without substantially reducing the image quality. Thus, software alone may be used to provide a desired magnification level of the real-time stereoscopic video image.

Figure 2:
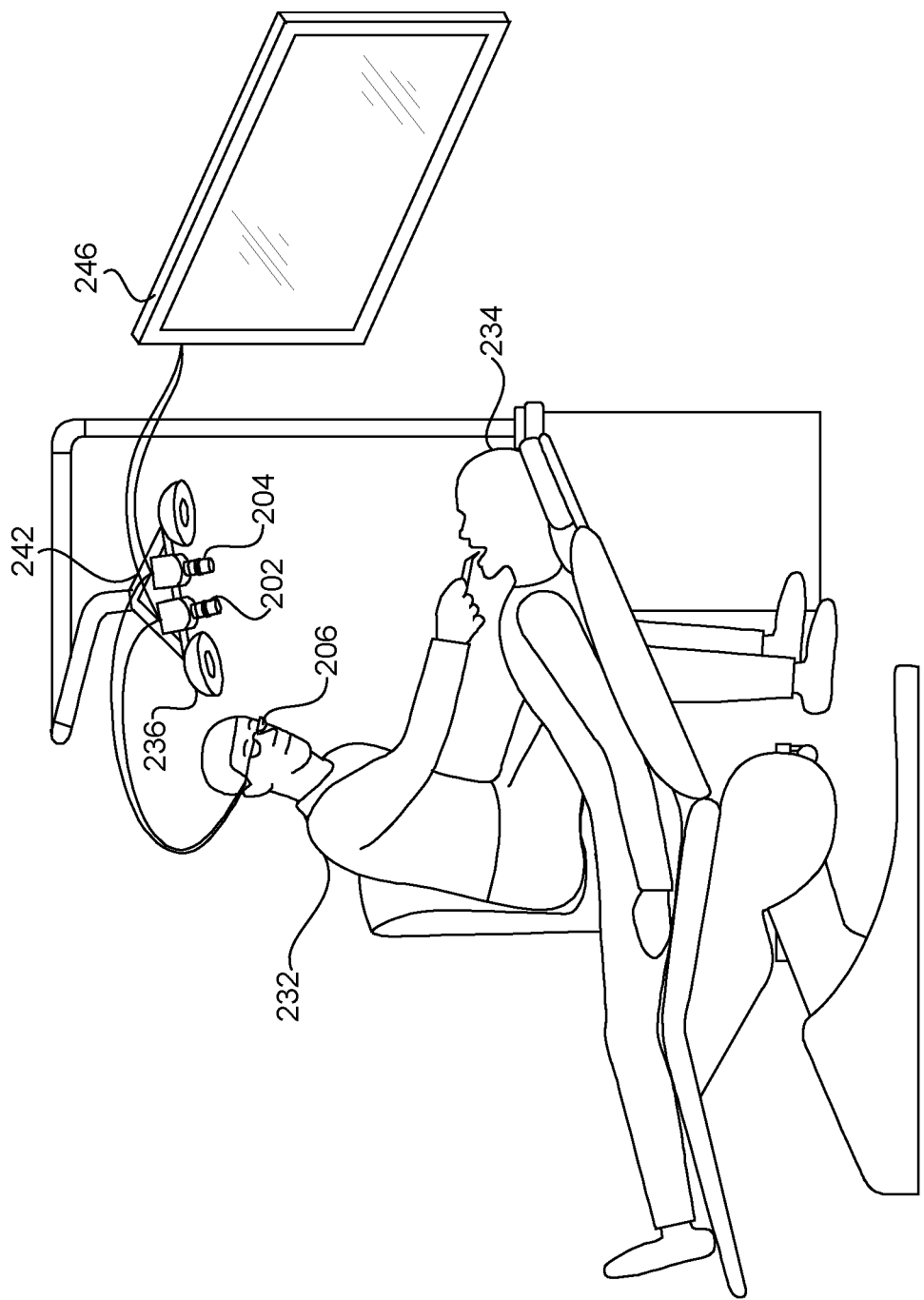
FIG. 2 provides an example illustration of a dentist using a stereoscopic display to view a near real-time stereoscopic video image of a patient's intraoral cavity in accordance with an alternative embodiment of the present disclosure.

FIG. 2 provides an example illustration of a dentist 232 using a head mountable stereoscopic display 206 to view a near real-time stereoscopic image of a patient's intraoral cavity in accordance with one embodiment of the present disclosure. The first video camera 202 and the second video camera 204 can be mounted on a fixture 242 above the patient 234.

A light 236, such as a dental light source, can be provided to illuminate the patient's intraoral cavity. The light can provide sufficient illumination to enable the first video camera 202 and the second video camera 204 to zoom to a desired magnification level while maintaining a selected depth of field for the near real-time stereoscopic video image. The depth of field can be selected to enable the dentist to have a clear, focused view of all of the desired locations within the patient's intraoral cavity. The aperture of the first and second video cameras may change when the magnification provided by the video cameras is increased. Alternatively, the light source may be sufficiently bright that no change in aperture is needed.

The depth of field of the first and second video cameras 202, 204 may be greater than a length of the patient's intraoral cavity. For example, if the depth of field of the first and second video cameras is twice the depth of a typical patient's intraoral cavity, then the first and second video cameras can be focused on the patient's lip while maintaining a clear focus to the back of the patient's mouth, assuming that the depth of field of the cameras is centered.

In one embodiment, the head mountable stereoscopic video display 206 can be configured to provide a split field of view, with a bottom portion of the glasses providing separate high definition displays for the left and right eyes, and above the glasses, the dentist can view the environment unencumbered. Alternatively, the glasses can be configured in a split view where the bottom half provides the video image, and the top half of the glasses is substantially transparent to enable an operator to view both natural surroundings while wearing the head mountable stereoscopic display. This can be especially useful as the dentist is using a high magnification level while working on the patient's mouth and can move quickly to no magnification when viewing the surrounding environment.

Alternatively, a video display other than the head mountable stereoscopic video display can be positioned to display the near real-time stereoscopic video image as well. For instance, a large television screen can be configured to show three dimensional images as well. The placement is based on a desired application, but in one embodiment, it may be placed behind the patient 234 in a position that enables the dentist 232 to view the video image. It can also be placed for the patient to view, or for students to view for learning in an educational environment, for example. The video display can be configured to enable viewers to view the stereoscopic display 246 as a three dimensional image, either with or without the assistance of eyewear.

For instance, in one embodiment the first and second video feeds can be displayed on a single display screen 246, with the respective video feeds being optically separated using at least one of shutter separation, polarization separation, and color separation. In one embodiment, a viewer, such as a dentist, can wear viewing glasses to view the separate images with stereopsis and depth perception.

Certain types of viewing glasses, such as LCD glasses using shutter separation, may be synchronized with the display screen to enable the viewer to view the optically separated near real-time stereoscopic video image. The optical separation of the video feeds provides a visual perception leading to the sensation of depth from the two slightly different video images projected onto the retinas of the two eyes, respectively, to create stereopsis. As previously discussed, the sensation of depth enables the dentist to maintain substantially the same hand-eye coordination that the dentist has learned during his or her practice as a dentist.

The stereoscopic video display 206 can also be used to view information pertaining to the patient. For instance, x-rays can be digitized and viewed on the video display. A patient's chart information can also be displayed. This can enable the dentist to quickly come up to speed on the patient's status. The dentist can also make comparisons between previous images and information contained in the patient's chart and the patient's current status. The images can also be used to educate the patient, dental assistants, and so forth.

In one embodiment, the fixture 242 can be hingeably mounted or otherwise height adjustable. The distance of the video cameras to the patient can be varied as desired. For instance, the video cameras may be positioned at a distance from about 5 inches to about 96 inches above the patient's intraoral cavity. As the distance between the video cameras and the patient changes, the angle at which the first video camera and the second video camera are directed relative to one another can be adjusted to maintain stereopsis of the near real-time stereoscopic video image.

Figure 3:
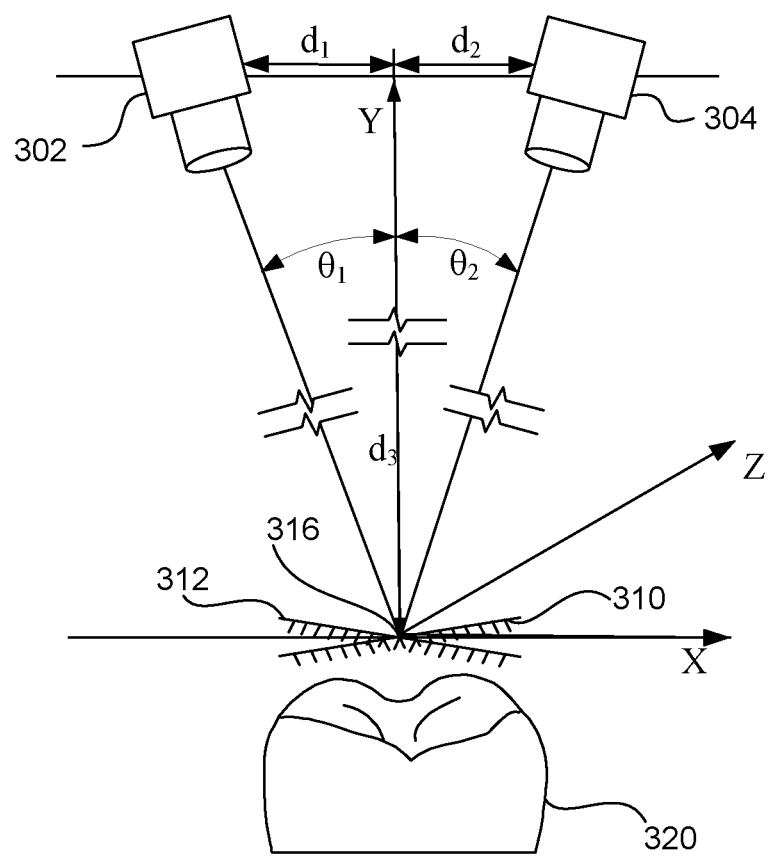
FIG. 3 provides an exemplary diagram illustrating how angles at which the first and second video cameras are directed and changed based on a distance of the video cameras from a selected object to maintain stereopsis of the video image in accordance with an embodiment of the present disclosure.

FIG. 3 provides an exemplary diagram illustrating how the angles of the first and second video cameras 302, 304 are related to a distance from an object. It should be noted that the illustration is not drawn to scale. The cameras can be separated by a selected distance, such as a pupilary distance, as previously discussed. In one embodiment, distance $d_1$ can be substantially equal to distance $d_2$. In this example, $d_1=d_2=30$ mm. However, the actual distance may vary based on system needs, e.g., $d_1+d_2=$a value in the range of about 50 mm to 75 mm.

In order to view a selected object 320 or area, such as a tooth in this example, the first video camera 302 is directed to the object at an angle $\theta_1$ with respect to a normal. The second video camera 304 can be directed to the object at an angle $\theta_2$ with respect to the normal. When the object is centered between the cameras 302, 304 then $\theta_1$ is substantially equal to $\theta_2$, though this is not necessarily required.

The first video camera 302 can create a video image of a first plane 310, based on the angle $\theta_1$. The second video camera 304 can create a video image of a second plane 312 based on the angle $\theta_2$. The first and second planes 310, 312 cross at a location referred to as a convergent point 316. In one embodiment, the convergent point can be selected to be positioned at approximately the location of the object 320. Alternatively, the convergent point may be selected to be within the depth of field of the cameras. When the image is magnified by zooming the first and second cameras, then the convergent point can be selected such that it is within the final, magnified video image.

As the distance $d_3$ between the cameras 302, 304 and the object 320 changes, the angles $\theta_1$ and $\theta_2$ can be adjusted such that the convergent point is maintained at approximately the same location. The distance of $d_3$ may change when a position of the fixture 242 of FIG. 2 is adjusted relative to the patient 234. The distance of $d_3$ may also change when the patient moves.

As previously discussed, a tracking point can be used to track movements of the patient. In one embodiment, the convergent point can be separate from the tracking point. For instance, the tracking point may be an optical marker on a patient's forehead and the convergent point can be the focus point on a patient's tooth. The convergent point can be correlated with the tracking point such that when the tracking point moves a certain amount in at least one of the x, y, and z axes, the convergent point can be moved approximately the same distance. Alternatively, the tracking point may be substantially equal to the convergent point. This allows the video feeds of a selected location that are created by the first and second video cameras 302, 304 to be maintained even when the patient moves, thereby enabling the dentist to maintain a view of the near real-time stereoscopic video image of the selected location.

Returning to FIG. 1a, the direction in which the first and second video cameras 102, 104 are positioned can be updated using at least one electric motor 112 that is mechanically coupled to each video camera. For instance, a single motor may be used to cause an angle of a video camera to be changed along a first axis, such as rotating the video camera. A second motor may be used to allow the video camera angle to be adjusted along a second axis. In one embodiment, two motors are sufficient to allow each video camera to be adjusted along an x and y axis to direct each video camera in a desired direction. However, a third motor may be used to allow the video camera's position to be adjusted along a third axis. The three motors can allow each video camera's position to be redirected along an x, y, and z axis to be directed in substantially any direction.

The at least one motor 112 can communicate with the tracking module 108 to update the position of the first and second video cameras. In one embodiment, a user can manually actuate the position of the first and second video cameras through the use of a software interface that is in communication with the at least one motor 112.

Once the video cameras 102, 104 are set in a desired direction, enabling the user to view a selected area, such as a patient's tooth, the location can be set as the convergent point. As previously discussed, the convergent point is associated with a selected tracking point. The position of the tracking point can be selected such that there is about a one to one movement of the tracking point in relation to the convergent point. For instance, an optical marker may be placed on a patient's forehead or somewhere else that is convenient for a given application. When the patient moves his or her head, the change in position of the forehead is generally substantially similar as the change in position of the patient's tooth (barring some sort of unnatural twisting movement that would be less likely while sitting in a dentist chair). Thus, when the tracking point moves, the position of the cameras can be updated relative to the movement of the tracking point to enable the convergent point to be maintained over the same selected area, such as the patient's tooth. The dentist may use an insert, such as a retractor inserted in the patient's oral cavity, so that the angle of opening of the jaw remains substantially unchanged. In one embodiment, when using a retractor, the tracking point can be placed thereon, or on another area close to or within the oral cavity, such as a tooth, lip, cheek, nose, chin, etc.

The position of the first and second video cameras 102, 104 can also be affected by physically changing their location relative to a patient. For instance, the cameras may be mounted on a fixture that can be rotated, raised and lowered, hingeably moved, or otherwise repositioned, as discussed in FIG. 2. When the position of the video cameras are changed by moving the fixture, then the at least one motor 112 can be used to redirect the video cameras to the selected area. In one embodiment, the position of the fixture can be used in conjunction with the motors to direct the video cameras in a desired direction. For instance, a dentist may position the fixture to provide desired lighting and align the video cameras with a patient's intraoral cavity to allow the video cameras to be directed to a desired location within the intraoral cavity.

Figure 1D:
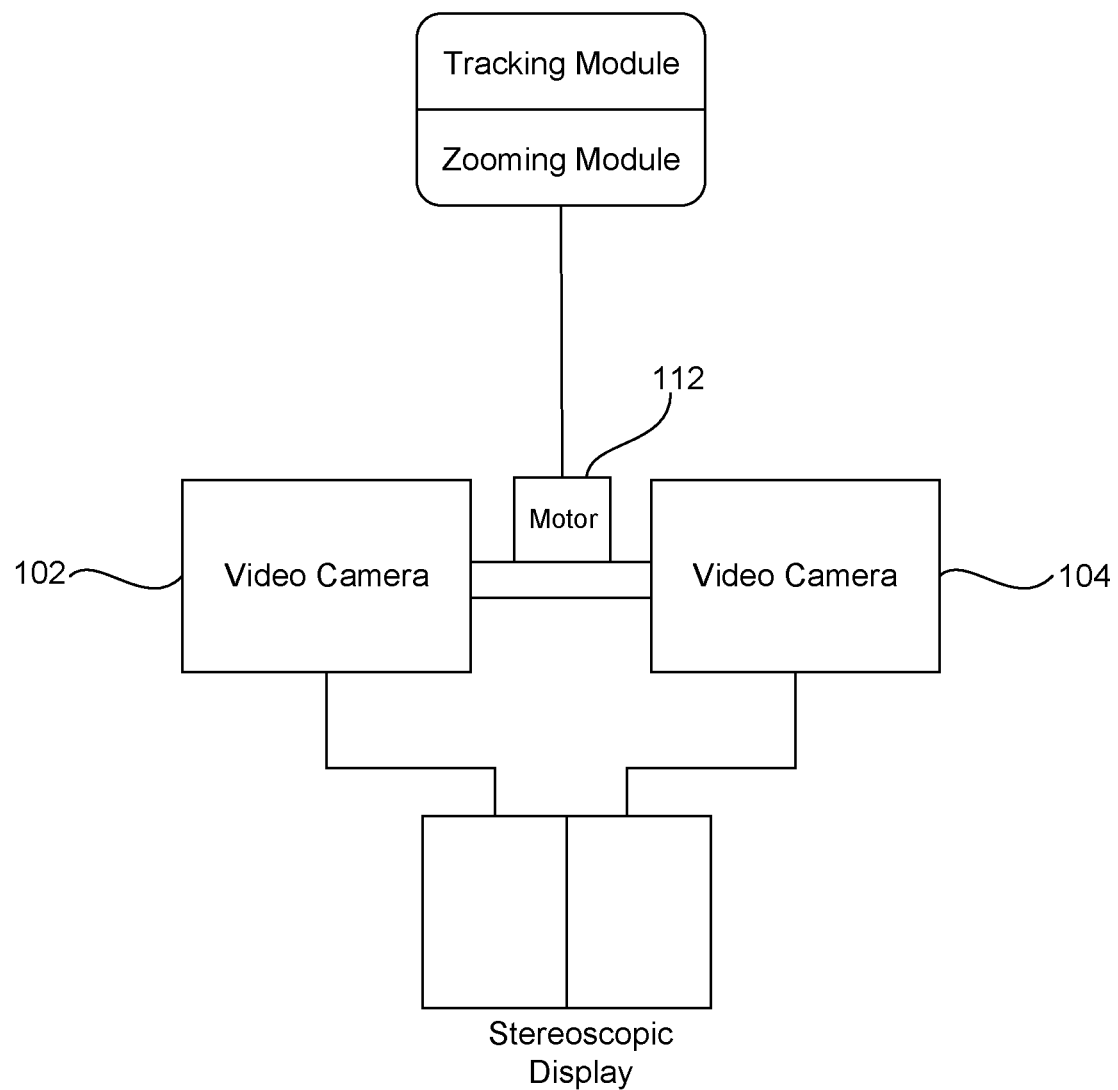
FIG. 1d illustrates a block diagram of a system for viewing stereoscopic video images with a single motor used to update a position of first and second video cameras in accordance with an embodiment of the present disclosure.

FIG. 1*d* provides an example illustration of another embodiment, wherein a single motor 112 is used to update a position of the first and second video cameras 102, 104. The single motor can be mechanically coupled to the first and second video cameras. For example, the motor may be connected through a series of gears and/or screws that allow the motor to be used to change an angle in which the video cameras 102, 104 are directed. Other types of mechanical couplings can also be used, as can be appreciated. Any type of mechanical coupling that enables the motor 112 to update a direction in which one or both of the first and second video cameras are pointed is considered to be within the scope of this embodiment.

Figure 4:
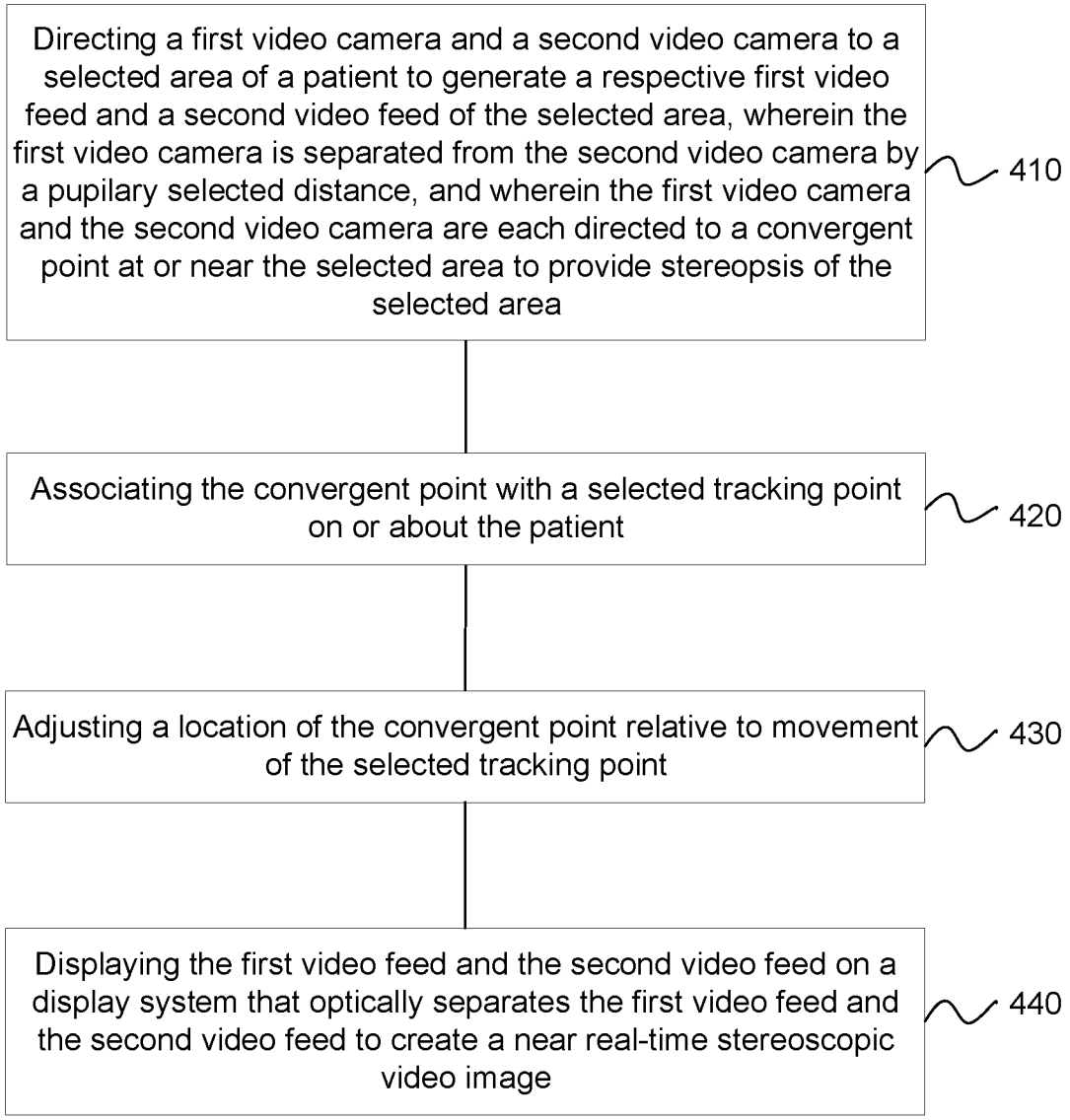
FIG. 4 depicts a flow chart of a method for viewing stereoscopic medical video images in accordance with an embodiment of the present disclosure.

In another embodiment, a method 400 for viewing stereoscopic medical video images is disclosed, as depicted in the flow chart of FIG. 4. The method includes directing 410 a first video camera and a second video camera to a selected area of a patient to generate a respective first video feed and a second video feed of the selected area. The first video camera is separated from the second video camera by a selected distance. In one embodiment, the selected distance can be a pupilary distance. Alternatively, a greater distance may be selected, as previously discussed. The first video camera and the second video camera are each directed to a convergent point at or near the selected area to provide stereopsis of the selected area.

The method 400 further comprises associating 420 the convergent point with a selected tracking point on or about a patient. The selected tracking point can include an optically trackable marker, as has been discussed. In one embodiment, the optically trackable marker may be positioned on a dental retractor located in or about the patient's intraoral cavity. Alternatively, the selected tracking point can include a plurality of wireless transceivers configured to triangulate a position of the selected tracking point based on the timing of signals received at a transceiver located at the tracking point relative to at least two other transceivers positioned on or about the patient.

For instance, in one embodiment, a surgical operating room may include four separate radio frequency transceivers positioned at different locations about the operating room. A tracking transceiver can then be placed on a patient entering the operating room. The tracking transceiver can send or receive signals from the transceivers located in the operating room. The timing of the signals between the tracking transceiver and the four transceivers in the operating room can be used to determine the position of the tracking transceiver in three dimensions using trigonometry, as can be appreciated.

The accuracy of the triangulation calculation is based, at least in part, on the frequency of the transceivers. Higher frequency transceivers have shorter wavelengths, thereby enabling a more accurate determination of the position of the tracking transceiver. Increased accuracy can also be obtained by merely tracking the change in movement. As the tracking transceiver moves closer to one of the transceivers in the room, and further from another, the resulting change in the timing of the signals can enable a substantially accurate determination of the change in position of the tracking transceiver.

The method 400 further comprises adjusting a location of the convergent point relative to movement of the selected tracking point. In one embodiment the convergent point can be selected as a virtual point that has an x, y, and z axis distance from the tracking point. When the tracking point is moved then the first video camera and the second video camera can be redirected to maintain a view of the selected area based on the change in the x, y, and z axis distance of the tracking point. For instance, once the convergent point has been selected relative to the tracking point, the tracking point may move 1 inch in each of the x, y, and z axes due to a movement of the patient on which the tracking point is located. It can be assumed that the convergent point has also been moved 1 inch in each of the x, y, and z axes and the position of the first and second video cameras can be redirected to the adjust the location of the convergent point to the new location.

The method 400 further comprises displaying the first video feed and the second video feed on a display system that optically separates the first video feed and the second video feed to create a near real-time stereoscopic video image. In one embodiment, the first video feed can be displayed on a right video display of a head mountable video display and the second video feed can be displayed on a left video display of the head mountable video display. The right and left video displays can be projected onto a user's right and left eyes, respectively. The stereoscopic video image provides a visual perception leading to the sensation of depth from the two slightly different video images projected onto the retinas of the two eyes.

Alternatively, the first video feed and the second video feed can be displayed on a single display wherein the first video feed and the second video feed are optically separated using at least one of shutter separation, polarization separation, and color separation, as previously discussed. Depending on the type of optical separation used, glasses may be used to enable a user to separate the image displayed on the single display to the first video feed being directed to the user's right eye and the second video feed being directed to the user's left eye, or vice versa.

The first video camera and the second video camera can each be zoomed to provide a desired level of magnification of a selected portion of the near real-time stereoscopic image. The rate at which the magnification changes for each of the first and second video cameras can be substantially equal to maintain the stereopsis of the stereoscopic video image. The final amount of magnification can also be substantially equal for the same reason. In addition to optically magnifying the stereoscopic video image using the first and second cameras, the video image can be further magnified using digital magnification, as can be appreciated.

In discussing the systems and methods of the present disclosure above, is also understood that many of the functional units described herein have been labeled as "modules," in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices, or the like.

Modules may also be implemented in software for execution by various types of processors. An identified module of executable code may, for instance, comprise one or more physical or logical blocks of computer instructions, which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. The modules may be passive or active, including agents operable to perform desired functions.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A stereoscopic video imaging and tracking system, comprising:
    a first video camera to generate a first video feed of a subject;
    a second video camera spaced a distance from the first video camera to generate a second video feed of the subject, wherein the first video camera and the second video camera are directed toward a convergent point to provide a stereoscopic image of the subject;
    a tracking system to cause the first video camera and the second video camera to follow a tracking point, wherein movement of the tracking point causes movement of the convergent point to maintain stereopsis of the subject; and
    a head mountable video display to display the stereoscopic image.

2. The system of claim 1, wherein the head mountable video display includes a right eye display and a left eye display for viewing by a user's right eye and left eye, respectively.

3. The system of claim 1, wherein the head mountable display provides a split field of view to enable an operator to view both natural surroundings and the stereoscopic video image while wearing the head mountable stereoscopic display.

4. The system of claim 1, wherein the first video feed and the second video feed are wirelessly communicated to the head mountable stereoscopic display.

5. The system of claim 1, wherein the first video feed and the second video feed are communicated to the head mountable stereoscopic display through a wired connection.

6. The system of claim 1, further comprising a chart viewing system to display one or more pages of a chart on the head mountable stereoscopic display.

7. The system of claim 1, wherein the subject is a patient in a medical setting.

8. The system of claim 1, wherein the patient is a dental patient, and the tracking point or the convergent point is at or about dental patient's intraoral cavity.

9. The system of claim 1, further comprising a zooming device associated with the first video camera and the second video camera, the zooming device to provide variable magnification of the stereoscopic video image to the head mountable display.

10. The system of claim 9, wherein zooming device causes the first video camera and the second video camera to zoom together, and wherein the zoom is at least one of an optical zoom or a digital zoom.

11. The system of claim 9, wherein zooming device causes the first video camera and the second video camera to each zoom and provide an image with a magnification power of at least about 4 times.

12. The system of claim 9, wherein zooming device causes the first video camera and the second video camera to each zoom and provide an image with a magnification power within a range from about 1 time to about 20 times.

13. The system of claim 1, wherein the first video camera and the second video camera are positioned at a distance from about 5 inches to about 96 inches from a location for the subject.

14. The system of claim 1, wherein the tracking point is an optically trackable marker configured to be positioned at the subject to enable a direction of the first video camera and the second video camera to be adjusted based on a change in a location of the optically trackable marker.

15. The system of claim 14, wherein the subject is a dental patient, and wherein the optically trackable marker is configured to be positioned on a dental retractor located in or about the patient's intraoral cavity.

16. The system of claim 14, wherein the optically trackable marker is configured to be placed on a body surface of the subject.

17. The method of claim 1, wherein the tracking point comprises at least two radio frequency markers and the convergent point is determined relative to the at least two radio frequency markers.

18. The system of claim 1, wherein the convergent point is a virtual point that has an x, y, and z axis distance from the tracking point.

19. The system of claim 1, wherein the convergent point is at the tracking point.

20. The system of claim 1, wherein the tracking point is a mobile marker configured to be located on a hand held instrument.

21. The system of claim 1, wherein at least one of the first video camera or the second video camera are coupled to a motor or multiple motors to enable an angle at which the first video camera and the second video camera are directed relative to one another to be changed, the angle to be changed based at least in part on a distance of the video cameras from the subject to maintain stereopsis of the stereoscopic video image independent of the distance.

22. The system of claim 1, further comprising a light source configured to provide illumination of the subject.

23. A stereoscopic video imaging and tracking system, comprising:
- a first video camera to generate a first video feed of a subject;
- a second video camera spaced a distance from the first video camera to generate a second video feed of the subject, wherein the first video camera and the second video camera are directed toward a convergent point to provide a stereoscopic image of the subject; and
- a tracking system to cause the first video camera and the second video camera to follow a tracking point to maintain stereopsis of the subject,
- wherein the convergent point is correlated with the tracking point such that when the tracking point moves in at least one of the x, y, and z axes, the convergent point moves approximately the same distance and a direction in correlation with movement of the tracking point.

24. The system of claim 23, wherein a location of the tracking point is substantially equal to a location of the convergent point.

25. The system of claim 23, wherein the convergent point is at the tracking point.

26. The system of claim 23, wherein the convergent point moves at about a one to one ratio with respect to direction and distance relative to movement of the tracking point.

27. The system of claim 23, wherein when the tracking point moves, positioning of the cameras is updated relative to the movement of the tracking point to enable the convergent point to be maintained relative to the tracking point.

28. The system of claim 23, wherein the tracking point is provided by an optically trackable marker to be positioned at the subject to enable a direction of the first video camera and the second video camera to be adjusted based on a change in a location of the optically trackable marker.

29. The system of claim 23, wherein the subject is a dental patient, and wherein the optically trackable marker is configured to be positioned on a dental retractor to be located in or about the patient's intraoral cavity.

30. The system of claim 23, wherein the optically trackable marker is configured to be placed on a body surface of the subject.

31. The method of claim 23, wherein the tracking point comprises at least two radio frequency markers and the convergent point is determined relative to the at least two radio frequency markers.

32. The system of claim 23, wherein the convergent point is a virtual point that has an x, y, and z axis distance from the tracking point and the convergent point is maintained in relation to the tracking point as the tracking point moves.

33. The system of claim 23, wherein the tracking point is a mobile marker configured to be located on a hand held instrument.

34. The system of claim 23, further comprising a stereoscopic video display to display the stereoscopic image to a user.

35. The system of claim 34, wherein the stereoscopic video display is a head mountable video display to display including a right eye display and a left eye display for viewing by the user's right eye and left eye, respectively.

36. The system of claim 23, wherein the subject is a patient in a medical or dental setting.

37. The system of claim 23, further comprising a zooming device associated with the first video camera and the second video camera, the zooming device to provide variable magnification of the stereoscopic video image to the head mountable display.

38. The system of claim 23, wherein the first video camera and the second video camera are positioned at a distance from about 5 inches to about 96 inches from a location for the subject.

39. The system of claim 23, wherein at least one of the first video camera or the second video camera are coupled to a motor or multiple motors to enable an angle at which the first video camera and the second video camera are directed relative to one another to be changed, the angle to be changed based at least in part on a distance of the video cameras from the subject to maintain stereopsis of the stereoscopic video image independent of the distance.

40. The system of claim 23, further comprising a light source configured to provide illumination of the subject.

* * * * *